US009326926B2

(12) United States Patent
Pressly et al.

(10) Patent No.: US 9,326,926 B2
(45) Date of Patent: *May 3, 2016

(54) KERATIN TREATMENT FORMULATIONS AND METHODS

(71) Applicant: Liqwd, Inc., Santa Barbara, CA (US)

(72) Inventors: Eric D. Pressly, Santa Barbara, CA (US); Craig J. Hawker, Santa Barbara, CA (US)

(73) Assignee: Liqwd, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/713,885

(22) Filed: May 15, 2015

(65) Prior Publication Data

US 2015/0328102 A1 Nov. 19, 2015

Related U.S. Application Data

(60) Provisional application No. 61/994,709, filed on May 16, 2014.

(51) Int. Cl.
*A61K 8/362* (2006.01)
*A61Q 5/08* (2006.01)
*A61Q 5/10* (2006.01)
*A61Q 5/12* (2006.01)
*A61K 8/41* (2006.01)
*A61Q 5/04* (2006.01)

(52) U.S. Cl.
CPC ............... *A61K 8/362* (2013.01); *A61K 8/416* (2013.01); *A61Q 5/08* (2013.01); *A61Q 5/10* (2013.01); *A61Q 5/12* (2013.01); *A61K 2800/882* (2013.01); *A61Q 5/04* (2013.01)

(58) Field of Classification Search
CPC ... A61K 2800/882; A61K 8/32; A61K 8/416; A61Q 5/04; A61Q 5/08; A61Q 5/10; A61Q 5/12
See application file for complete search history.

(56) References Cited

U.S. PATENT DOCUMENTS

| | | | |
|---|---|---|---|
| 2,850,351 A | 9/1958 | Moore | |
| 3,142,623 A | 7/1964 | Zviak | |
| 3,840,656 A | 10/1974 | Kalopissis | |
| 4,240,450 A | 12/1980 | Grollier | |
| 4,425,132 A † | 1/1984 | Grollier | |
| 4,532,950 A | 8/1985 | Lang | |
| 4,812,307 A | 3/1989 | Siuta-Mangano | |
| 5,350,572 A | 9/1994 | Savaides | |
| 5,656,265 A | 8/1997 | Bailey | |
| 5,811,085 A | 9/1998 | Halloran | |
| 5,833,966 A | 11/1998 | Samain | |
| 6,458,906 B1 | 10/2002 | Torgerson | |
| 6,537,532 B1 | 3/2003 | Torgerson | |
| 6,706,258 B1 | 3/2004 | Gallagher | |
| 6,984,250 B1 * | 1/2006 | Legrand et al. | 8/401 |
| 7,041,142 B2 | 5/2006 | Chan | |
| 7,390,479 B2 | 6/2008 | Sockel | |
| 7,598,213 B2 | 10/2009 | Geary | |
| 8,298,519 B2 | 10/2012 | Adams | |
| 2006/0024257 A1 | 2/2006 | Chang | |
| 2008/0066773 A1 | 3/2008 | Anderson | |
| 2008/0138309 A1 | 6/2008 | Malle | |
| 2008/0141468 A1 | 6/2008 | Cotteret | |
| 2008/0187506 A1 | 8/2008 | Carballada | |
| 2009/0126756 A1 | 5/2009 | Syed | |
| 2010/0004391 A1 | 1/2010 | Haddleton | |
| 2010/0202998 A1 | 8/2010 | Ramos-Stanbury | |
| 2011/0256084 A1 | 10/2011 | Dixon | |
| 2013/0172518 A1 | 7/2013 | Huang | |
| 2013/0309190 A1 | 11/2013 | Dimotakis | |
| 2015/0034119 A1 * | 2/2015 | Pressly et al. | 132/286 |

FOREIGN PATENT DOCUMENTS

| | | |
|---|---|---|
| DE | 1220969 | 7/1966 |
| DE | 10051773 | 4/2002 |
| DE | 10051774 | 4/2002 |
| DE | 102004052480 | 5/2006 |
| EP | 0299764 | 1/1989 |
| EP | 0298684 | 4/1993 |
| EP | 0978272 | 2/2000 |
| EP | 1174112 | 1/2002 |
| EP | 1779896 | 5/2007 |
| EP | 2295029 | 3/2011 |
| GB | 773559 | 4/1957 |
| KR | 1020060059564 | 6/2006 |
| WO | WO 9300882 A1 * | 1/1993 |
| WO | 9308787 | 5/1993 |
| WO | 9501152 | 1/1995 |
| WO | 0232383 | 4/2002 |
| WO | 0232386 | 4/2002 |
| WO | 2011134785 | 11/2011 |
| WO | 2012080321 | 6/2012 |

(Continued)

OTHER PUBLICATIONS

Dombrink and Tanis, "pH & hair shampoo", Chem Matters, p. 8 (1983).

(Continued)

*Primary Examiner* — Abigail Fisher
(74) *Attorney, Agent, or Firm* — Pabst Patent Group LLP

(57) ABSTRACT

Formulations, kits, and methods for rebuilding the disulfide bonds in keratin found in hair, skin, or nails. Hair that is damaged due to a hair coloring treatment and/or other reducing treatment, such as during a permanent wave, can be treated with the formulations containing one or more active agents. The formulations may be applied subsequent to a hair coloring treatment or simultaneously with a hair coloring treatment. Use of the active agent formulations during a permanent wave treatment prevents the reversion of the hair to its previous state, for at least one week, preferably at least three months, more preferably at least one year, most preferably greater than one year, after one or more than one application of the formulation. Application of the active agent formulation to skin or nails can help repair damaged disulfide bonds due to natural wear and tear or natural aging.

17 Claims, No Drawings

(56) References Cited

FOREIGN PATENT DOCUMENTS

| WO | 2012084532 | 6/2012 |
|---|---|---|
| WO | 2012164064 | 12/2012 |
| WO | 2014016407 | 1/2014 |
| WO | WO 2014118212 A1 * | 8/2014 |
| WO | 2014167508 | 10/2014 |
| WO | 2015017768 | 2/2015 |
| WO | 2015026994 | 2/2015 |

OTHER PUBLICATIONS

Hall and Wolfram, "Application of the theory of hydrophobic bonds to hair treatments", J Soc Cosmet Chem., 28:231-41 (1977).
International Search Report and Written Opinion for PCT/US2014/049388 mailed Oct. 29, 2014.
Koval, "Reactions of Thiols", Russian J Organic Chemistry, 43(3):319-49 (2007).
Majonis, et al., "Dual-purpose polymer labels for fluorescent and mass cytometric affinity bioassays", Biomacromolecules, 14(5):1503-13 (2013).
Salvin, et al. "Biological surface modification by thiol-ene\ addition of polymers synthesized by catalytic chain transfer polymerization (CCTP)", Polymer Chem., 3:1461-6 (2012).
Shansky, "Dyeing of Human Hair with Fiber Reactive Dyestuffs", Cosmetics and Toiletries (1976).
Shansky, "The Reaction Mechanism of Fiber Reactive Dyestuffs with Hair Keratin", American Perfumer and Cosmetics (1966).
Thermo FisherScientific, "Bismaleimide Crosslinkers (BMOE, BMB and BMH)", product instructions, pp. 1-3 (2012).
Combined Search and Examination Report mailed Sep. 14, 2015 in connection with related UK patent application, GB1513932.2.
Mintel Leave-in Hair and Scalp Nutrient, XP002743522, Database accession No. 10141004, Jun. 1, 2003.
Mintel Permanent Hair Colour, XP002743523, Database Accession No. 2061070, May 1, 2013.
Partial International Search Report for corresponding PCT application PCT/ US2015/031166mailed Sep. 14, 2015.
WPI Abstract Accession No. 1995-355152, English Abstract of JPH 07242520, Sep. 19, 1995, retrieved Feb. 2, 2016.
Combined Search and Examination Report for GB 1523109 mailed Feb. 4, 2016.
International Search Report for related PCT application, PCT/US2015/031166, mailed Jan. 22, 2016.
Third part observation for GB 1513932.2 (2016).

* cited by examiner
† cited by third party

KERATIN TREATMENT FORMULATIONS AND METHODS

CROSS-REFERENCE TO RELATED APPLICATIONS

This application claims priority to U.S. Provisional Application Ser. No. 61/994,709, filed May 16, 2014, the disclosure of which is incorporated herein by reference in its entirety.

FIELD OF THE INVENTION

The present invention generally relates to formulations and methods for treating keratin in hair, skin, or nails, and in particular for strengthening and/or repairing hair during or after a coloring or permanent wave treatment.

BACKGROUND OF THE INVENTION

Hair coloring is currently a globally accepted fashion phenomenon. Color treatments include hair coloring, highlighting, and bleaching. The coloring products can be categorized in several types, which include permanent, demi-permanent, semi-permanent, and temporary coloring formulations. Permanent hair coloring products make up the majority of the market worldwide.

Significant effort has been directed towards developing various approaches to hair dyeing; these include, oxidative dyes, direct action dyes, natural dyes, metallic dyes and reactive dyes. Many hair coloring formulations, in particular permanent coloring formulations, use reducing agents to break the disulfide bonds in the hair allowing deeper penetration of the hair coloring dyes and bleaching agents into the hair.

Disulfide bond linkages in hair are also broken by application of reducing agents, such as during permanent wave and hair straightening process. After the disulfide bonds are broken, the hair is placed in stress to establish the final style (e.g., straight, wavy, or curly), and the disulfide bonds are re-established.

Thioglycolic acid, particularly as the ammonium salt, is often used to cleave the cysteine disulfide bonds present in hair. Sodium bisulfite is another example of a known reducing agent commonly used in various dyes and bleaching agents in color treatments.

Typically, oxidation to restore the reduced bond is partially obtained when an oxidizing agent, such as hydrogen peroxide is present in a coloring formulation and/or by exposing the hair to atmospheric oxygen. However, this oxidation step can be very slow and can leave the hair frizzy and damaged.

Similarly, hair undergoing a permanent wave treatment is typically treated with a reducing agent followed by an oxidizing agent. Hydrogen peroxide is optionally added in a second step to restore the hair to its prior state. The newly formed disulfide bonds of the treated hair are under stress to maintain the hair's new shape; thus, they break easily resulting in a reversion of the hair style over time.

The use of peroxides in the hair styling process can result in damaged hair, removal of non-natural color from the hair, and/or leave the hair frizzy. Furthermore, some latent reduced thiols may remain in the hair even after oxidative treatment. Hair styling treatments with peroxides involve the following reaction with thiol groups:

$$2K-S-H+H_2O_2 \rightarrow K-S-S-K+2H_2O \quad \text{(Reaction I)}$$

where K represents keratin in the hair.

In the case where two K—S—H groups are not present for Reaction I to take place, it is believed that the following reaction takes place, which results in damaged hair:

$$K-S-H+H_2O_2 \rightarrow K-SO_2-OH \quad \text{(Reaction II)}.$$

In addition to being a major component in hair, keratin is also a major component in skin and nails. There are a number of different types of keratin and they are generally grouped as soft or hard keratins. Soft keratins are more prevalent in skin, while hard keratins predominate in hair and nails. Nails, in particular, are made of a modified keratin similar to that found hair. The disulfide bonds of the keratin in nails contribute to their impermeability. Therefore, damage to the disulfide bridges of keratin present in skin or nails can result in unhealthy and/or flaky skin or nails. Maintaining the disulfide bridges of keratin therefore helps to keep skin healthy and prevents cracking and splitting in nails.

Substantial improvement is needed in the areas of color saturation, color development, precise initial color consistency, improved wash fastness, and improved hair conditioning when applying color treatments. For example, the attainment of precise initial colors that are retained by the hair for a desirable time period has remained an elusive goal. The coloring formulations also cause severe hair damage, especially when coloring treatments are repeated. Moreover, various standard daily actions to the hair, for example hair brushing, hair blow-drying, and sun light exposure can cause even more damage to the hair.

Similar damage to the hair can also result from permanent wave treatments. In both coloring and permanent wave processes, improvements are also needed to repair damage and/or to strengthen the hair during or after such styling treatments. Additionally, improved treatments and methods are needed which can be applied to skin and nails to repair damaged keratin.

There is a need for hair formulations and treatments that repair and/or strengthen keratin in hair damaged from coloring and/or permanent wave treatments using reducing treatments.

There is also a need for hair formulations and treatments that can repair latent reduced thiols present in hair.

There is also a need for formulations and treatments that can repair damage to keratin present in skin and hair.

Therefore, it is an object of this invention to provide improved formulations and methods for repairing and/or strengthening damaged hair.

It is also an object of this invention to provide methods for using formulations that repair and/or strengthen hair after and/or during coloring or permanent wavetreatments.

It is also an object of this invention to provide formulations and methods for using these formulations to repair and/or strengthen hair after a reducing treatment.

It is also an object of this invention to provide formulations and methods for using these formulations that repair and/or strengthen keratin in hair, skin or nails due to natural wear and tear or due to natural aging.

SUMMARY OF THE INVENTION

Formulations, kits, and methods for restoring hair that has been broken during a hair coloring or permanent wave treatment are disclosed. The formulations have similar benefits when used with different color chemical processes, such as bleaching, highlights, lowlights, semi-permanent, demi-permanent, and permanent color. Improved methods of styling hair, for example permanent hair waving and hair curling are also provided. The formulations can be applied each time the hair is washed or daily, once-weekly, twice-weekly, biweekly, once-monthly, every other month, or at less frequent intervals. Preferably, the formulations are applied once-monthly to achieve the desired results.

Traditional methods of permanent hair waving, hair curling, or straightening use hydrogen peroxide after a reducing treatment. The process generally takes about three days to complete. The methods disclosed herein use active agents to repair the hair; these active agents are washed from the individual's hair on the same day that they are applied to the hair. Under the same conditions, such as temperature and moisture, hair treated with the formulations disclosed herein takes a longer time to revert to its prior state as compared to the same hair that is treated with hydrogen peroxide.

The formulations disclosed herein contain one or more polyfunctional compounds. The polyfunctional compound contains at least one ionizable functional group capable of forming ionic bonds, and the polyfunctional compound also contains at least one functional group capable of forming a covalent bond with a thiol group. In some embodiments, the polyfunctional compounds contains at least two ionizable groups. Optionally, the formulation is applied at the same time as the hair coloring or permanent wave treatment. Alternatively, the formulation may be applied after the hair coloring or permanent wave treatment or to damaged hair. For example, the formulations can be applied within one week of the hair being treated and/or damaged, preferably within three days, more preferably within two days, most preferably immediately after application of the coloring or permanent wave treatment.

DETAILED DESCRIPTION OF THE INVENTION

I. Definitions

The term "hair" refers to one or more than one strand of hair, as well as the natural components of hair, such as oil from a body. Hair also refers to virgin hair or processed hair, for example hair that has been exposed to hair waving or hair straightening formulations.

"Pharmaceutically acceptable" and "cosmetically acceptable" are used interchangeably and refer to those compounds, materials, and/or formulations, which are, within the scope of sound medical judgment, suitable for use in contact with the tissues of human beings and animals without excessive toxicity, irritation, allergic response, or other problems or complications commensurate with a reasonable benefit/risk ratio. More specifically, pharmaceutically acceptable refers to a material, compound, or formulation that is suitable for use in contact with the skin, scalp, or hair. Pharmaceutically acceptable materials are known to those of ordinary skill in the art.

"Shampoo", as used herein, generally refers to a liquid or semi-solid formulation applied to hair that contains detergent or soap for washing the hair.

"Conditioner", as used herein, generally refers to a formulation (e.g., liquid, cream, lotion, gel, semi-solid) applied to hair to soften the hair, smooth the hair, and/or change the sheen of the hair.

"Analog" and "derivative" are used herein interchangeably, and refer to a compound that possesses the same core as the parent compound, but differs from the parent compound in bond order, the absence or presence of one or more atoms and/or groups of atoms, or a combination thereof. The derivative can differ from the parent compound, for example, in one or more substituents present on the core, which may include one or more atoms, functional groups, or substructures. In general, a derivative can be formed, at least theoretically, from the parent compound via chemical and/or physical processes.

"Electrophilic group" or "electrophilic moiety" are used interchangeably and refer to one or more functional groups or moieties that have an affinity for or attract electrons.

"Nucleophilic group" or "nucleophilic moiety" are used interchangeably and refer to one or more functional groups or moieties that are electron rich and are capable of reacting with electrophilic groups.

"Michael acceptor", as used herein, is a species of electrophilic groups or moieties that participates in nucleophilic addition reactions. The Michael acceptor can be or can contain an $\alpha,\beta$-unsaturated carbonyl-containing group or moiety, such as a ketone. Other Michael acceptors include pi-bonds, such as double or triple bonds conjugated to other pi-bond containing electron withdrawing groups, such as nitro groups, nitrile groups, and carboxylic acid groups.

"Carboxylic acid," as used in here refers to the group —COOH. Unless specified otherwise the term carboxylic acid embraces both the free acid and carboxylate salt.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulthydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms, in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted," as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms, such as nitrogen, may have hydrogen substituents and/or any permissible substituents of organic compounds described herein that satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Polymer", as used herein, refers to a molecule containing more than 10 monomer units.

"Water-soluble", as used herein, generally means at least 50, 75, 100, 125, 150, 200, 225, or 250 g is soluble in 1 L of water at 25° C.

II. Formulations

The formulation and methods disclosed herein are concerned with treating keratin in hair, skin, or nails. In one embodiment, the methods relate to strengthening and/or repairing hair after it has undergone a coloring treatment or after or during a permanent wave treatment. Additionally, the formulations may reduce or prevent hair damage due to hair coloring and/or bleaching processes.

A. Formulations

The formulations contain one or more polyfunctional compounds (also referred to herein as "active agents").

The active agents can be combined with one or more pharmaceutically acceptable carriers and/or excipients that are considered safe and effective to human hair and/or human scalp, and may be administered to an individual's hair without causing undesirable biological side effects, such as burning, itching, and/or redness, or similar adverse reactions. The formulations may further contain an excipient that renders the formulations neutral pH, or a pH ranging from about pH 3 to about pH 12, preferably from pH 5 to pH 8.

The active agent is typically present in an amount ranging from about 0.01 wt % to about 50 wt % of the formulation, preferably from about from about 1 wt % to about 25 wt % of the formulation, more preferably from about 1 wt % to about 15 wt %, most preferably from about 1 wt % to about 10 wt %. Typically, the active agent may be present in an amount ranging from about 0.5 to about 3 wt % of the formulation, or from about 1 to about 3 wt % of the formulation.

The active agent is stable in aqueous solution for a period of at least 2, 3, 4, 5, 6, 8, 9, 10, 11, or 12 months or longer at pH of 6 to 8 and a temperature of about 25-30° C., preferably about 25° C. "Stable" as used herein with respect to shelf-life means that at least 40, 45, 50, 55, 60, 65, 70, 75, 80, 85, 90, or 95% of the compound is unchanged over the specified period.

a. Active Agents

The active agent is a polyfunctional compound that may contain ionizable functional groups capable of forming ionic bonds and functional groups capable of forming a covalent bond with a thiol. Suitable ionizable functional groups include, but are not limited to, acidic groups such as carboxylic acids, sulfonic acids, phosphonic acids, and basic groups, such as amines Suitable functional groups capable of forming a covalent bond with a thiol include, but are not limited to, Michael acceptors, alkyl halides or sulfonate esters.

The active agent may have the following Formula I:

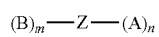

Formula I wherein Z is a linker or is absent, m and n are each an integer independently selected from 0-6, provided that m+n is at least 2, B is a functional group capable of forming a covalent bond with a thiol, and A is an ionizable functional group. In some embodiments, ionizable group A can be independently selected from the group consisting of: —COOH, —SO$_3$H, —PO$_3$H$_2$, and —N(R$^1$)$_2$; wherein R$^1$ is independently selected from the group consisting of a hydrogen, alkyl, alkenyl, alkynyl, cycloalkyl, aryl, heterocycloalkyl and heteroaryl groups; wherein each R$^1$ is independently unsubstituted or substituted with one or more substituents. In some other embodiments, ionizable group A can be an ionic group, such as —N$^+$(R$^1$)$_3$. In some preferred embodiments, each R$^1$ is independently selected from a methyl, ethyl, or isopropyl group.

Exemplary active agents according to Formula I may contain thiol reactive functional groups, as group B, for example, such as those shown in the following moieties:

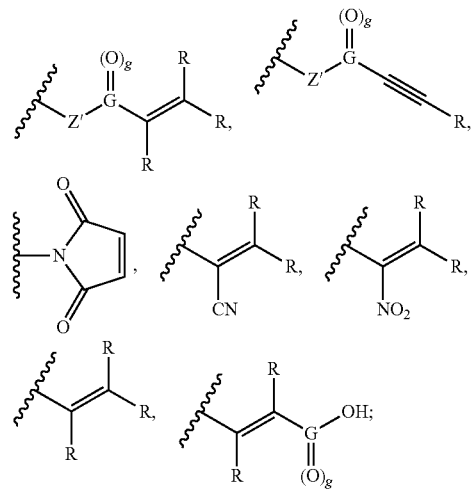

wherein R is independently selected from hydrogen, C$_{1-6}$ alkyl, aryl, or an ionizable functional group; Z' is oxygen (O), NH, or is absent; and G is carbon (C) and g is 1, or G is sulfur (S) and g is 2.

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may optionally be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, carboxylate (—COO—), primary amide (e.g., —CONH$_2$), secondary amide (e.g., —CONHR$_{11}$), —C(O)NR$^1$R$^2$, —N NR$^1$C(O) R$^2$, —S(O)$_2$R$^2$, —SR$^1$, and —S(O)$_2$NR$^1$R$^2$, sulfonyl group (e.g., —SOR$_1$), and sulfonyl group (e.g., —SOOR$_1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In certain preferred embodiments, the linker Z is a C$_{1-10}$ alkyl group which may be unsubstituted or substituted one or more times by oxo, hydroxyl, carboxyl, amido or amino. Preferably, the linker Z is a C$_{1-4}$ alkyl group. The alkyl group may be linear or branched. The alkyl group may also be interrupted one or more times by a heteroatom selected from oxygen, sulfur and nitrogen. An example of such a di-carboxylic acids having a heteroatom interruption is thiodipropionic acid. In other embodiments, the alkyl group may contain one or more double or triple bonds.

In some embodiments, the active agent of Formula I has one of the following structures:

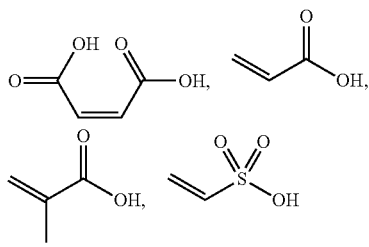

or is a simple salt of these structures.

In certain other embodiments, the active agent may have the following Formula II:

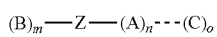

Formula II wherein Z is a linker or is absent, m and n are each an integer independently selected from 0-6, provided that m+n is at least 2, B is a functional group capable of forming a covalent bond with a nucleophile, such as but not limited to a thiol or amine group, A is an ionizable functional group as defined above, and C contains an ionic group and a functional group which is also capable of forming a covalent bond with a nucleophile, such as but not limited to a thiol or amine group, and which has a charge opposite to that of ionizable group A. Group C is ionically bonded (denoted by dashed line) to group A. For ionic group C, o is an integer value independently selected from 0-6, such that the sum of charges of group C and ionizable group A is zero. In some embodiments, ionizable group A can be independently selected from the group consisting of: —COOH, —SO$_3$H, —PO$_3$H$_2$, and —N(R$^1$)$_2$; wherein R$^1$ is independently selected from the group consisting of a hydrogen, alkyl, alkenyl, alkynyl, cycloalkyl, aryl, heterocycloalkyl and heteroaryl groups; wherein each R$^1$ is independently unsubstituted or substituted with one or more substituents. In some other embodiments, ionizable group A can be an ionic group such as —N$^+$(R$^1$)$_3$. In some preferred embodiments, each R$^1$ is independently selected from a methyl, ethyl, or isopropyl group.

The active agents according to Formula II may contain thiol reactive functional groups as group B, for example, such as those shown in the following moieties:

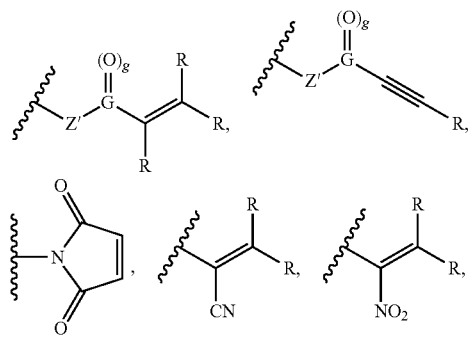

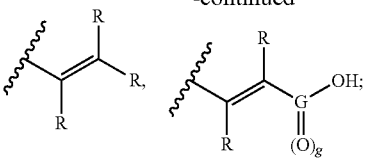

wherein R is independently selected from hydrogen, C$_{1-6}$ alkyl, aryl, or an ionizable functional group; Z' is oxygen (O), NH, or is absent; and G is carbon (C) and g is 1, or G is sulfur (S) and g is 2.

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may optionally be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, carboxylate (—COO—), primary amide (e.g., —CONH$_2$), secondary amide (e.g., —CONHR$^1$), —C(O)NR$^1$R$^2$, NR$^1$R$^2$, —NR'S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$_1$), and sulfonyl group (e.g., —SOOR$^1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In certain preferred embodiments, the linker Z is a C$_{1-10}$ alkyl group which may be unsubstituted or substituted one or more times by oxo, hydroxyl, carboxyl, amido or amino. Preferably, the linker Z is a C$_{1-4}$ alkyl group. The alkyl group may be linear or branched. The alkyl group may also be interrupted one or more times by a heteroatom selected from oxygen, sulfur and nitrogen. An example of such a di-carboxylic acids having a heteroatom interruption is thiodipropionic acid. In other embodiments, the alkyl group may contain one or more double or triple bonds.

Group C is an ionic group ionically bonded to ionizable group A and contains at least one thiol reactive selected from a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinimide group, a sulfinamide group, a sulfonimidate group, or a sulfonimidamide group.

In some embodiments, the active agent of Formula II has one of the following structures:

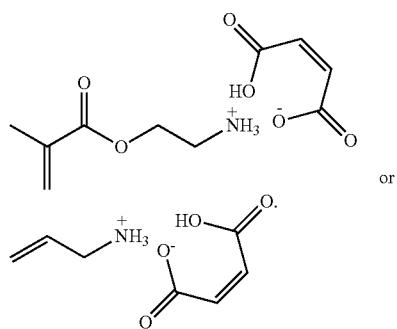

b. Excipients

The formulations typically contain one or more cosmetically acceptable excipients. Cosmetically acceptable excipients include, but are not limited to preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

The formulations typically contain at least two cosmetically acceptable excipients. In some forms, the formulations contain the active agent, water, and optionally a preservative and/or fragrance.

The formulation for treating hair may be in any suitable physical foul'. Suitable forms include, but are not limited to low to moderate viscosity liquids, lotions, milks, mousses, sprays, gels, creams, shampoos, conditioners, and the like. Suitable excipients, such as those listed above, are included or excluded from the hair care formulation depending on the form of use of the formulation (e.g., hair spray, cream, conditioner, or shampoo).

The pharmaceutical excipient is typically present in an amount ranging from about 10 wt % to about 99.99 wt % of the formulation, preferably about 40 wt % to about 99 wt %, more preferably from about 80 wt % to about to about 99 wt %.

i. Surfactants

Surfactants are surface-active agents that are able to reduce the surface tension of water and cause the hair formulation to slip across or onto the skin or hair. Surfactants also include detergents and soap. The surfactants may be amphoteric, anionic, or cationic. Suitable surfactants that may be used in the formulation include, but are not limited to, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium $C_{12-15}$ alkyl sulfate, ammonium $C_{12-15}$ pareth sulfate, ammonium $C_{12-16}$ alkyl sulfate, ammonium $C_{9-10}$ perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol or ceteareth-20, or combinations thereof.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

More than one surfactant may be included in the formulation.

The surfactants are optionally included in an amount ranging from about 0.1% to about 15% by weight of the formulation, preferably about 1% to about 10% by weight of the founulation.

ii. Emollients

Emollient refers to a material that protects against wetness or irritation, softens, soothes, coats, lubricates, moisturizes, protects, and/or cleanses the skin. Suitable emollients for use in the formulations include, but are not limited to, a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or combinations thereof. More than one emollient may be included in the formulation.

The emollient is optionally included in an amount ranging from about 0.5% to about 15% by weight of the formulation, preferably from about 1% to about 10% by weight of the formulation.

iii. Emulsifiers

The formulation may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, polysorbate-80, or combinations thereof. More than one emulsifier may be included in the formulation.

The emulsifier is optionally included in an amount ranging from about 0.05%-15% by weight of the formulation, preferably from about 0.1%-10% by weight of the formulation.

iv. Preservatives

One or more preservatives may be included in the formulation. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the formulation. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium—15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.1% to about 5% by weight of the formulation, preferably from about 0.3% to about 3% by weight of the formulation. Preferably, the formulations are paraben free.

v. Conditioning Agents

One or more conditioning agents may be included in the formulation. Suitable conditioning agents include, but are not limited to, silicone-based agents (e.g., silicone quaternium-8), panthenol, hydrolyzed wheat and/or soy protein, amino acids (e.g. wheat amino acids), rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

The conditioning agent(s) is optionally included in an amount ranging from about 0.1% to about 5% by weight of the formulation, preferably from about 0.3% to about 3% by weight of the formulation.

vi. Diluents

Diluent, as used herein, refers to a substance(s) that dilutes the active agent. Water is the preferred diluent. The formulation typically contains greater than one percent (by wt) water, preferably greater than five percent (by wt) water, more preferably greater than 50% (by wt) water, and most preferably greater than 80% (by wt) water. Alcohols, such as ethyl alcohol and isopropyl alcohol, may be used at low concentrations (about 0.5% by weight of the formulation) to enhance hair penetration and/or reduce odor.

vii. Viscosity Modifying Agents

The formulations may contain one or more viscosity modifying agents, such as viscosity increasing agents. Classes of such agents include, but are not limited to, viscous liquids, such as polyethylene glycol, semisythetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

viii. Antioxidants

The formulation may contain one or more antioxidants. Examples include, but are not limited to, tocopheryls, BHT, ascorbic acid, *camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

ix. Opacifying Agents

The formulation may contain one or more opacifying agents. Opacifying agents are added to the formulations to make it opaque. Suitable opacifying agents include, but are not limited to, glycol distearate and ethoxylated fatty alcohols.

c. Forms of the Formulation i. Sprays

The formulation may be in the food of a spray. The spray typically includes the active agent and a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. Preferably, the spray formulation includes a preservative. In some embodiments, the formulation includes a fragrance. In some embodiments, the formulation includes a surfactant. In some embodiments, the formulation contains water, fragrance, a preservative, and an active agent. In some embodiments, the formulation contains water, fragrance, a preservative, and an active agent. In some embodiments, the formulation contains water, a preservative, fragrance, an active agent, and an anti-static agent. In some embodiments, the formulation contains water, a preservative, fragrance, an active agent, and a hair conditioning agent. In some embodiments, the formulation contains water, a preservative, fragrance, an active agent, and a surfactant.

The hair spray formulations may be dispensed from containers that include aerosol dispensers or pump spray dispensers. Such dispensers are known in the art and are commercially available from a variety of manufacturers.

Propellant

When the hair spray formulation is dispensed from a pressurized aerosol container, a propellant may be used to force the formulation out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the formulation to the hair.

ii. Conditioners

The formulation may be in the form of a conditioner. The conditioner typically includes the active agent in a suitable carrier. Additionally, the conditioner may include cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the formulation, and/or a conditioning action (deposition on the surface of the skin or the hair).

The active agent may be included in any suitable concentration. Typical concentrations of active agent in the conditioner range from small amounts such as approximately 0.01% (by wt), preferably at least 0.1% (by wt), to large amounts, such as up to 50% (by wt). Preferably the conditioner contains the active agent in a concentration ranging from 0.1% (by wt) to 5% (by wt), more preferably from 0.1% wt to 3% (by wt). While greater concentrations of active agent could be present in the conditioner, they are generally not needed to achieve the desired results.

iii. Shampoos

The hair repair formulation may be in the form of a shampoo. The shampoo typically includes the active agent in a suitable carrier. The active agent may be included in any suitable concentration. Typical concentrations of the active agent in the shampoo range from small amounts such as approximately 0.01% (by wt), preferably at least 0.1% (by wt), to large amounts, such as up to 50% (by wt). Preferably the shampoo contains the active agent in a concentration ranging from 0.1% (by wt) to 5% (by wt), more preferably from 0.1% (by wt) to 3% (wt). While greater concentrations of active agent could be present in the shampoo, they are generally not needed to achieve the desired results.

Additionally, the shampoo may include from about 0.5% to about 20% by weight of a surfactant material. Surfactants utilized in shampoo compositions are well-known in the art and are disclosed, for example, in U.S. Pat. No. 6,706,258 to Gallagher et al. and U.S. Pat. No. 7,598,213 to Geary et al.

iv. Creams, Lotions, Gels, and Polish

The hair, skin, or nail repair formulation may be in the form of a cream, lotion, gel, or polish. The cream, lotion, gel, or polish typically includes the active agent in a suitable carrier. The active agent may be included in any suitable concentration. Typical concentrations of the active agent in the cream, lotion, gel, or polish range from small amounts such as approximately 0.01% (by wt), preferably at least 0.1% (by wt), to large amounts, such as up to 50% (by wt). Preferably the cream or lotion contains the active agent in a concentration ranging from 0.1% (by wt) to 5% (by wt), more preferably from 0.1% (by wt) to 3% (by wt). While greater concentrations of active agent could be present in the cream or lotion, they are generally not needed to achieve the desired results.

Additionally, the formulation, depending on use, may include an oil, a hair conditioning agent, and/or a thickening agent. The cream, lotion, gel, or polish may also include a fragrance, a plant extract, and/or a surfactant. The cream, lotion, gel, or polish may be packaged in a tube, tub, bottle, or other suitable container.

v. Liquid Active Agent Formulations

In some embodiments, a liquid active agent formulation is provided, which is mixed at the time of use with a second formulation, such as a coloring or highlighting formulation. In these embodiments, the liquid active agent formulation may contain any suitable concentration of active agent in a suitable carrier, typically a diluent, such as described above. The concentration of the active agent is suitable to provide a mixture with the appropriate final volume and final concentration of active agent.

For example, a liquid active agent formulation can contain a concentration of active agent ranging from about 5% (by wt) to about 50% (by wt) or greater. In a preferred embodiment, the liquid active agent formulation contains about 20% (by wt) active agent.

For highlighting applications, prior to use, a sufficient volume of a liquid active agent formulation is mixed with a sufficient volume of a highlighting formulation to form a highlighting mixture having the desired concentration of active agent. Typical concentrations of the active agent in the highlighting mixture range from small amounts, such as approximately at least 0.01% (by wt), preferably at least 0.1% (by wt), to large amounts, such as up to 50% (by wt). Preferably the highlighting mixture contains the active agent in a concentration ranging from 0.1% (by wt) to 5% (by wt), more preferably from 0.1% (by wt) to 3% (wt). While greater concentrations of active agent could be present in the highlighting mixture, they are generally not needed to achieve the desired results.

III. Methods of Use

A. Treatment of Hair with Coloring Agents a. Apply the Coloring Formulation to the Hair The coloring formulation is generally applied to an individual's hair following normal hair coloring procedures that are known to those skilled in the art. Typically, hair color treatments include two complementary processes: applying a bleaching formulation to bleach the hair's natural pigment and/or other artificial pigments present in the hair, and diffusion of dye precursors into the hair, followed by coupling reactions that result in the formation of chromophores within the hair shaft, which are too large to diffuse out of the hair. The bleaching formulation typically contains a bleaching agent to lighten the hair and produce free thiol groups. The hair coloring formulation may be a highlighting formulation, such as formed by mixing bleach powder and developer. More complex colors may contain several precursors and many couplers, and may involve multiple reactions.

The dye precursors may contain several ingredients, each with different functions. The first ingredient is usually an alkalizing agent (usually ammonia and/or an ammonia substitute, such as monoethanolamine [MEA]). The alkalizing agent serves a number of roles in the hair colorant process including swelling the hair fiber to aid in diffusion of the dye precursors. The dye precursors generally include p-diamines and p-aminophenols. Precursors are oxidized to active intermediates once they have penetrated the hair shaft. Intermediates then react with color couplers to create wash resistant dyes. More specifically, the intermediates, in the presence of an oxidant, couple with another oxidation dye intermediate molecule to form a large fused ring color compound within the hair shaft. The precursor intermediate should penetrate the hair shaft prior to the coupling reaction since the fused ring product is too large to penetrate the hair shaft. Couplers modify the color produced by the oxidation of precursor compounds. The primary difference between demi-permanent and permanent products is the alkalizing agent and the concentration of peroxide. The cuticle does not swell as greatly with demi-permanent dyes, making dye penetration less efficient compared to permanent coloring products.

Several coloring formulations use a reducing agent, such as sodium bisulfate, to break disulfide bonds in the hair, allowing deeper penetration of the hair coloring dyes into the hair. Specifically, the method includes reducing some of the disulfide linkages of the cystine in the hair shafts to thiol groups while breaking hydrogen bonds. The reducing process changes the chemical and cosmetic characteristics of the hair, which are undesirable.

The hair dyeing process may be followed by a shampoo and conditioning treatment, a neutralizing rinse or an acid balanced shampoo containing in addition to cationic or amphoteric surfactants, cation-active emollients and quarternary polymers. Alternately, the hair dying process may be followed by application of the active agent formulations described herein, before a shampoo and/or conditioning treatment.

b. Apply the Active Agent Formulation to the Hair

The active agent formulation may be applied simultaneously with the hair coloring formulation or subsequently to the application of the hair coloring formulation. For example, the active agent formulation may be mixed with the hair coloring treatment and the mixture, containing both the active agent and the hair coloring treatment, may be applied to the hair.

Alternatively, subsequent to coloring the hair, the active agent formulation, or a formulation thereof is applied to the hair. Although the active agent is typically applied on the same day as the coloring treatment, it may be applied later such as within 1 to 2 weeks following treatment with the reducing agent. Typically, the amount of active agent formulation (or a mixture of the active agent formulation and the hair coloring formulation) applied is sufficient to saturate the hair. The active agent may be applied to the hair as a single application, or application of the active agent may be repeated one or more times. Typically, the amount of active agent formulation applied in each application is sufficient to saturate the hair. The volume of active agent formulation applied to the hair in each application may be about 1 to about 100 mL per person depending on their length and volume of hair. In some embodiments, application of the active agent could be repeated immediately (e.g. within 10 to 15 seconds) or approximately 1, 5, 7.5, 10, 12.5, 15, 17.5, or 20 minutes after the first application.

The active agent can be rinsed and shampooed from the hair immediately following application, for example within 10, 15, 25, 30, 45, or 60 seconds, or two, three, four, or five minutes after application. Alternatively, the active agent may be rinsed from the hair within about 30 minutes following application, preferably between about 5 minutes and about 20 minutes, more preferably about 10 minutes after application of the active agent to the hair, depending on hair type.

If the active agent formulation is combined with the hair coloring treatment and applied as a mixture to the hair, then the mixture remains on the hair as long as needed for the hair coloring treatment. Typically the mixture is applied for approximately 10 minutes. The mixture is removed from the hair in accordance with standard methods for hair coloring treatments, e.g., rinse and shampoo, approximately 10 minutes after applying the mixture.

The active agent formulation is rinsed from the hair after its application. The hair may be rinsed and subsequently washed immediately (e.g. within 10 to 15 seconds following application) after the final application of the active agent. Preferably, the hair is rinsed and/or washed about 10 minutes or later after the final application of the active agent, such as about 15 minutes to about 30 minutes, optionally about 20 minutes after repeated application of the active agent to the hair.

The active agents are generally washed from the individual's hair on the same day as they are applied. In contrast, traditional perms which use only hydrogen peroxide (and do not involve the addition of the active agent) are generally not washed for at least 48 hours following application (washing the hair prior to 48 hours following a traditional permanent treatment may result in significant loss in the amount of curl in the hair and/or cause damage to the hair).

The formulation described herein improves hair quality, such as appearance (e.g., sheen) and feel, and decreases hair breakage when the hair is subjected to treatments, such as coloring or permanent waving.

In some embodiments, hair breakage decreases by 5, 10, 15, 20, 25, 30, 35, 40, 45, or 50% or higher after treatment with the active agent compared to untreated hair from the same individual. Hair breakage is a significant problem encountered during coloring and other treatments.

B. Chemical Treatment of Hair with a Reducing Agent

In one embodiment, prior to treatment with the active agent, the hair has been subjected to a reducing agent used for waving (also referred to herein as hair perming or permanent waves), and/or curling of the hair.

a. Apply a reducing agent to the hair

The first step in waving or curling hair is breaking the cysteine disulfide bonds to form free thiol moieties. The process for breaking the cysteine disulfide bonds is via application of a reducing agent. The process for applying the reducing agent involves following normal perming or hair straightening procedures that are known to those skilled in the art. For example, to perm hair, the hair is first washed and set on perm rods of various sizes. Second, a reducing agent, such as thioglycolate reducing solution or lotion is applied to the hair. The hair is allowed to set for a specified period of time, and then the thioglycolate solution is rinsed from the hair.

The application of hydrogen peroxide in this process is optional. In some processes, such as when treating previously chemically treated hair, hydrogen peroxide is generally not used. In other processes, such as when perming virgin hair, hydrogen peroxide may be added. In these embodiments, hydrogen peroxide is typically added after the reducing agent is rinsed out. Then the hydrogen peroxide is rinsed from the hair prior to adding the active agent.

b. Apply the active agent Subsequent to the reducing treatment, one or more of the active agent, or a formulation thereof is applied to the hair. Although the agent is typically applied on the same day as treatment with the reducing agent, it may be applied later such as within 1 to 2 weeks following treatment with the reducing agent.

Typically, the amount of active agent formulation applied is sufficient to saturate the hair. The agent is generally rinsed and shampooed from the hair after the desired level of hair waving or curling is achieved. In some embodiments, the active agent is rinsed from the hair immediately (e.g. within 10, 15, 25, 30, 45, or 60 seconds following application) following the final application of the active agent. Alternatively the hair may be rinsed and washed about within about 30 minutes following application, preferably between about 5 minutes and about 20 minutes, more preferably about 10 minutes after the final application of the active agent to the hair, depending on the hair type. The active agent can be rinsed from the hair within 10, 15, 25, 30, 45, 60 seconds from the hair after application, and still achieve a desired level of hair waving or curling.

The active agent may be applied to the hair as a single application, or application of the agent may be repeated one or more times. Typically, the amount of active agent formulation applied in each application is sufficient to saturate the hair. In some embodiments, the volume of active agent formulation applied to the hair in each application is about 1 to about 10 mL per perm rod. In some embodiments, application of the active agent could be repeated immediately (e.g. within 10 to 15 seconds) or approximately 1, 5, 7.5, 10, 12.5, 15, 17.5, or 20 minutes after the first application. In some embodiments, the second application is about 7 minutes to about 10 minutes after the first application.

The active agent is rinsed from the hair after its application. The hair may be rinsed and washed immediately (e.g. within 10 to 15 seconds following application) after final application of the active agent. Alternatively the hair may be rinsed and washed about 10 minutes or later after the final application of the active agent, such as about 15 minutes to about 30 minutes, preferably about 20 minutes after repeated application of the active agent to the hair.

The active agents are generally washed from the individual's hair on the same day as they are applied. In contrast, traditional perms which use only hydrogen peroxide (and do not involve the addition of the active agent) are generally not washed for at least 48 hours following application (washing the hair prior to 48 hours following a traditional permanent treatment may result in significant loss in the amount of curl in the hair and/or cause damage to the hair).

The formulations described herein can be applied to hair to improve hair quality, such as appearance (e.g., sheen) and feel, and decrease hair breakage when the hair is subjected to subsequent treatments, such as coloring.

In some embodiments, hair breakage decreases by 5, 10, 15, 20, 25, 30, 35, 40, 45, or 50% or higher after application of the active agent compared to untreated hair from the same individual. Hair breakage is a significant problem encountered during coloring and other treatments.

C. Treatment of Skin or Nails with the Active Agent

In one embodiment, a formulation containing one or more of the active agents is applied to the skin or nails. Application of the active agent formulation to skin or nails can help repair damaged disulfide bonds due to natural wear and tear or natural aging.

In some embodiments the active agent formulation is in the form of a cream or lotion, which is suitable for application to the skin or nails. In other embodiments, the active agent formulation is in the form of a gel or polish, which is suitable for application to the nails. Typically, the amount of active agent formulation applied is sufficient to treat the damaged keratin in the skin or nails. The active agent formulation may be applied to the skin or nails in a single application, or application of the formulation may be repeated one or more times, as needed, to achieve the desired effect of repairing keratin damage and/or strengthening the skin or nails.

IV. Kit

Kits for treating hair are provided. In one embodiment, the kit typically contains a first formulation for coloring hair. The hair coloring formulation typically include a reducing agent capable of reducing disulfide bonds in hair to produce free thiol groups. The kit also includes a second formulation containing an effective amount of the active agent.

The kit may further include a developer bottle, gloves, shampoo, conditioner, and/or an odor eliminator. Instructions for use of the kit are also typically provided.

Typically the kit contains more than one container (or more than one compartment in a given container) to ensure that the lightening agent (e.g., peroxides) or the coloring agent is stored separately from the active agent.

A. First Formulation

The first formulation in the kit can be a coloring treatment. The first formulation may be formulated as two or more components which may be mixed together before application to the hair. For example, the first formulation may be in the form of two components such as a dye precursor and an oxidant. Typically, the hair coloring formulation contains a reducing agent capable of reducing the disulfide bonds in hair and producing reduced free thiol groups. Suitable reducing agents include, but are not limited to, thioglycolic acid, thiolactic acid, dihydrolipoate, thioglycerol, mercaptopropionic acid, sodium bisulfite, ammonium bisulfide, zinc formaldehyde sulfoxylate, sodium formaldehyde sulfoxylate, sodium metabisulfite, potassium borohydride, pegylated thiols and hydroquinone. The amount of the reducing agent in the first formulation is sufficient to rupture a sufficient number of disulfide bonds for effective diffusion of the hair coloring ingredients as would be appreciated by one of skill in the art.

The components of the first formulation may differ depending on the hair coloring treatment desired (such as for semi-permanent, demi-permanent, or permanent hair color), the texture of the hair, the sensitivity of the user's skin, and such the like. Hair coloring formulations for different hair coloring treatment, hair texture, and hair sensitivity are known to those of skill in the art.

B. Active agent formulation

The second formulation contains one or more active agents in an effective amount. Suitable formulations containing the active agents are discussed above. The second formulation may be in any suitable form. Suitable forms include, but are not limited to, low to moderate viscosity liquids, lotions, milks, mousses, sprays, gels, creams, shampoos, conditioners, and the like. The second formulation will be present in a suitable container, which depends on the form of the formulation.

In one embodiment, the active agent formulation is provided as two or more separate ingredients. For example, the active agent may be provided as a dry powder in a sealed package and the excipient provided in a vial or other container. A suitable mixing container for the active agent and the excipient may be provided.

In some embodiments, the active agent formulation (or second formulation) is mixed with the first formulation (or hair coloring treatment), and the mixture is applied to the hair.

C. Other Materials in the Kit

The kit optionally contains shampoos and conditioners. Suitable shampoos and conditioners include, but are not limited to LiQWd® Hydrating Shampoo and LiQWd® Hydrating Conditioner.

The kit may further contain an odor eliminator. The odor eliminator can be incorporated into the first or second formulation, or a mixture thereof. Alternately, the odor eliminator is present in a suitable container for use before or after washing the second formulation from the hair. Some suitable odor eliminators are known to those of ordinary skill in the art.

It is understood that the disclosed method and formulations are not limited to the particular methodology, protocols, and reagents described as these may vary. It is also to be understood that the terminology used herein is for the purpose of describing particular embodiments only, and is not intended to limit the scope of the present invention which will be limited only by the appended claims.

EXAMPLES

Example 1

Color Retention and Texture of Colored Hair Treated with the Active Agent Formulation

General

Three hair samples were obtained from a human subject and cut in ½ inch wide wefts.

Coloring formulation: The permanent hair coloring formulation was obtained from a L'Oreal® permanent hair coloring service (L'Oreal® Majirel permanent color #10 with 20 volume peroxide).

Active agent formulation: Maleic acid, at a concentration of 200 mg in 10 g total solution (water) was used.

Methods

The hair samples were washed with a clarifying shampoo then towel dried. The samples were then colored with the L'Oreal® permanent hair color service, which was left on the hair samples for approximately 35-40 minutes.

The first color treated hair sample ("control") was subsequently rinsed and washed with Liqwd® Hydrating Shampoo and Conditioner five times before being photographed.

The active agent formulation was applied to the second and third color treated hair samples via a spray bottle and massaging using the fingers. The active agent formulation was left on the second hair sample for a period of about 1 minute and on the third sample for a period of about 10 minutes. The hair samples were subsequently rinsed, and then washed with Liqwd® Hydrating Shampoo and Conditioner five times before being examined.

Results:

The hair samples treated with the active agent formulation showed better color retention, more shine, and less frizz than the control. The hair samples treated with the active agent formulation felt smoother to the touch and combined with the lower frizz and added sheen gave an overall healthier appearance over the control.

Example 2

Comparison of Color Retention in Traditionally Permed Hair and Hair Permed Using the Active Agent Formulations

Method

A ½ inch wide weft of hair sample, obtained from a human subject, was washed with clarifying shampoo then towel dried. Ammonium thioglycolate or dithiothreitol was mechanically pulled through the hair with a wide and a fine toothcomb several times then left on the hair for 10 minutes to 1 hour. The hair was then rinsed for 30 seconds to 1 minute with water, and then towel dried.

The active agent formulation, described in Example 1 (Maleic acid in water), was then applied via a needle nose applicator drenching the hair and leaving it on for 7.5 minutes. This step was repeated, for a total of 15 minutes. The hair was then rinsed for 1-2 minutes, shampooed, and then conditioned with various salon shampoo and conditioner brands, including LiQWd® Hydrating Shampoo and Hydrating Conditioner.

A second sample of hair was straightened, as described above, but using hydrogen peroxide instead of the active agent formulation. The hair samples were washed and conditioned repeatedly.

Comparison of Hair Color:

After both hair samples were washed five times using LiQWd® Hydrating Shampoo and LiQWd® Hydrating Conditioner, the samples were examined for their color retention.

Results

The hair sample treated with the active agent formulation displayed a color closer in intensity to the hair sample prior to the first washing, compared to the hair treated with hydrogen peroxide.

Example 3

Comparison of Hair Treated with Highlighting Formulation Applied Simultaneously with Active Agent Formulation and Hair Treated with Highlighting Formulation Alone

The active agent formulation in Example 1 contained maleic acid at concentrations of 2.0 g in 10 g total solution (water).

Two swatches of human hair were tested. A sample was taken from the same head, 1 inch wide, and split in half. The color was medium brown and had been previously color treated with an unknown professional hair color.

Swatch 1, ½ inch wide and 8 inches long, was lightened with traditional highlighting ingredients mixed with the active agent formulation. 1 oz of Joico Verocolor Veroxide developer-20 volume was mixed with 1 oz Joico Verolight powder bleach to form the highlighting formulation. Then 9 mL of the active agent formulation was added to the highlighting formulation to form a mixture.

The mixture was applied on the Swatch 1 hair with an applicator brush as the hair lay on aluminum foil. The foil was then wrapped around the swatch and allowed to process for 35 minutes. The swatch was rinsed and shampooed one time.

Swatch 2, the control, ½ inch wide and 8 inches long, was lightened with traditional highlighting ingredients in the absence of the active agent formulation. 1 oz of Joico Verocolor Veroxide developer-20 volume was mixed with 1 oz Joico Verolight powder bleach to form a highlighting formulation with a creamy consistency.

The highlighting formulation was applied on the Swatch 2 hair with an applicator brush as the hair lay on aluminum foil. The foil was then wrapped around the swatch and allowed to process for 35 minutes. The swatch was rinsed and shampooed one time.

Results

A noticeable difference in hair quality between Swatch 1 and Swatch 2 was observed. Swatch 1 hair was softer, less frizzy, appeared hydrated, with more shine than the control, Swatch 2.

Both swatches were washed and conditioned 5 more times with the same noticeable benefits of Swatch 1 (treated with the mixture of highlighting formulation and active agent formulation) compared to the control, Swatch 2 (treated with highlighting formulation, alone).

Example 4

Comparison of Hair Treated with Bleaching Formulation Applied Simultaneously with Active Agent Formulation and Hair Treated with Bleaching Formulation Alone General Two hair samples were obtained from a human subject and cut in ½ inch wide wefts.

Methods (1) 0.5 ounces of powder lightener (Clairol Professional, Basic White) and 0.5 ounces of conditioning cream developer (Redken, Blonde Icing) were combined to form a bleaching mixture. 3.5 g of 2-(methacryloyloxy)ethan-1-aminium (Z)-3-carboxyacrylate (12 wt % in water) was added to the bleaching mixture and thoroughly mixed with a brush.

(2) The bleaching mixture prepared was brushed onto the swatches of hair with a brush in order to thoroughly coat the strands of hair. The mixture coated hair was wrapped in aluminum paper and allowed to stand under ambient conditions for a period of two hours.

(3) After the two hour bleaching period the swatches of hair were washed with shampoo and the hair was subsequently allowed to air dry.

Results

A noticeable difference in hair quality between Swatch 1 and Swatch 2 was observed. Swatch 1 hair was demonstrated no discernible breakage, great feel, and a healthy appearance while the control (treated with bleaching formulation, alone) showed some breakage, had a rough feel, and was frayed with an unhealthy appearance.

Example 5

Comparison of Hair Treated with Bleaching Formulation Applied Simultaneously with Active Agent Formulation and Hair Treated with Bleaching Formulation Alone General Two hair samples were obtained from a human subject and cut in ½ inch wide wefts.

Methods (1) 0.5 ounces of powder lightener (Clairol Professional, Basic White) and 0.5 ounces of conditioning cream developer (Redken, Blonde Icing) were combined to form a bleaching mixture. 3.5 g of prop-2-en-1-aminium (Z)-3-carboxyacrylate (10 wt % in water) was added to the bleaching mixture and thoroughly mixed with a brush.

(2) The bleaching mixture prepared was brushed onto the swatches of hair with a brush in order to thoroughly coat the strands of hair. The mixture coated hair was wrapped in aluminum paper and allowed to stand under ambient conditions for a period of two hours.

(3) After the two hour bleaching period the swatches of hair were washed with shampoo and the hair was subsequently allowed to air dry.

Results

A noticeable difference in hair quality between Swatch 1 and Swatch 2 was observed. Swatch 1 hair was demonstrated no discernible breakage, great feel, and a healthy appearance while the control (treated with bleaching formulation, alone) showed some breakage, had a rough feel, and was frayed with an unhealthy appearance.

Example 6

Comparison of Traditional Perm Versus Perm Using Maleic Acid

General

Hair samples were obtained from a human subject and cut in ½ A inch wide wefts.

Reducing Agents: Ammonium thioglycolate (ATG) was obtained from a permanent wave kit manufactured by Zotos. 300 mg of Dithiothreitol in a 10 g solution was also used as the reducing agent.

Active Agent Formulation: Maleic acid at a concentration of 200 mg in 10 g total solution (water) was used.

Methods

Method for Perming Hair Using the Active Agent

The hair was washed with clarifying shampoo, towel dried, and then rolled around a perm rod. Ammonium thioglycolate or dithiothreitol was then applied to the hair and left on the hair for 10 minutes to 1 hour. The hair was then rinsed for 30 seconds to 1 minute and then blotted dry with a towel.

The active agent formulation was applied to the hair, via a needle nose applicator, drenching the hair. The active agent formulation was left on the hair for a period of about 7.5 minutes. The hair was drenched for a second time with the active agent formulation and left for a second 7.5 minutes, for a total of 15 minutes. The hair was then rinsed with water for about 1-2 minutes then unrolled from the perm rods. After the hair was removed from the peen rods, the hair was shampooed and conditioned with various salon shampoo and conditioner brands, including LiQWd® Hydrating Shampoo and Hydrating Conditioner. The washing and drying steps were repeated 40 times.

A second portion of hair was permed as described above, except, hydrogen peroxide was used instead of the active agent formulation.

Results

Both perms (utilizing the active agent formulation or hydrogen peroxide) showed only slight reduction in the overall curl after 40 cycles of washing and drying with the same shampoo and conditioner. However, the appearance and texture of the perm using the active agent formulation showed more sheen and less frizz compared to the perm using hydrogen peroxide.

Example 7

Comparison of Hair Breakage Due to Repeated Application of Traditional Perm and the Active Agent Formulation Methods Two hair samples were obtained. Both samples were treated with dithiothreitol or ammonium thioglycolate as described in Example 4. One of the hair samples was subsequently treated with the active agent formulation (Maleic acid in water), while the other was neutralized with hydrogen peroxide. The process was completed the same day for the hair treated with the active agent formulation. The process was completed in three days with hydrogen peroxide (traditional perm).

The procedure was repeated three times for each hair sample over a 48 hour time period.

Results

Upon visual inspections, the second hair sample treated with the active agent formulation showed little or no signs of breakage. However, the first hair sample treated with hydrogen peroxide showed significant breakage.

Example 8

Comparison of the Extent of Damage to Hair Previously Relaxed with a Japanese Relaxer Methods Two samples of hair, the first previously straightened with a Japanese relaxer (Yuko), and the second previously straightened with a no lye relaxer (African Pride Miracle Deep Conditioning) were obtained. The samples were treated as described in Examples 4 and 5 using the active agent formulation (Maleic acid in water).

Another hair sample, previously straightened with a no lye relaxer (African Pride Miracle Deep Conditioning) was obtained. The sample was treated with a traditional hair straightening perm (Zotos).

Results

The hair samples treated with the active agent formulation showed no noticeable damage. However, the sample treated with a traditional perm showed significant breaking, even during application.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for bleaching hair comprising:
   (a) applying to the hair a first formulation comprising a bleaching agent; and
   (b) applying to the hair a second formulation comprising an active agent, wherein the second formulation does not contain a coloring agent,
   wherein the active agent has the formula:

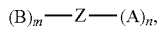

wherein Z is a linker or is absent;
   m and n are each an integer independently selected from 1-6, and the sum of m+n is equal to or greater than 2;
      wherein A and B are covalently bonded to Z when Z is present;
      B is a functional group capable of forming a covalent bond with a thiol or amine group and B is independently selected from the group consisting of:

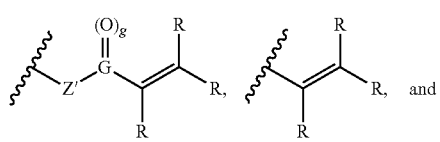

-continued

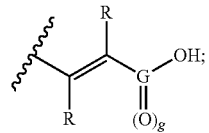

wherein R is independently selected from the group consisting of hydrogen, $C_{1-6}$ alkyl groups, aryl groups, or an ionizable functional groups and Z' is oxygen (O), NH or is absent, and G is carbon (C) and g is 1, or G is sulfur (S) and g is 2; and
      A is an ionizable functional group which is independently selected from the group consisting of: —COOH, —$SO_3H$, —$PO_3H_2$, —$N(R^1)_2$, —$N(R^1)_3$; wherein $R^1$ is independently selected from the group consisting of a hydrogen, alkyl, alkenyl, alkynyl, cycloalkyl, aryl, heterocycloalkyl and heteroaryl groups; wherein each $R^1$ is independently unsubstituted or substituted with one or more substituents; and
   wherein step (a) occurs simultaneously with step (b).

2. The method of claim 1, wherein the linker Z is an alkyl group, alkenyl group, cycloalkyl group, cycloalkenyl group, aryl group, heterocycloalkyl group, or heteroaryl group,
   wherein the alkyl, alkenyl, cycloalkyl, cycloalkenyl, aryl, heterocycloalkyl, or heteroaryl group, is unsubstituted or substituted one or more times by a halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —$C(O)R^1$, —$C(O)OR^1$, (—$COO^-$), primary amide, secondary amide, —$C(O)NR^1R^2$, —$NR^1R^2$, —$NR^1S(O)_2R^2$, —$NR^1C(O)R^2$, —$(O)_2R^2$, —$SR^1$, —$S(O)_2NR^1R^2$, —$SOR^1$, or —$SOOR^1$;
   wherein $R^1$ and $R^2$ are each independently selected from the group consisting of a hydrogen, alkyl group, alkenyl group, alkynyl group, cycloalkyl group, aryl group, heterocycloalkyl, and heteroaryl group, wherein each of $R^1$ and $R^2$ is independently unsubstituted or substituted with one or more substituents.

3. The method of claim 1, wherein the linker Z is a $C_{1-4}$ alkyl group.

4. The method of claim 3, wherein the alkyl group is substituted with one or more substituents replacing a hydrogen on one or more carbons of the alkyl hydrocarbon backbone or the alkyl group is substituted with one or more heteroatoms within the hydrocarbon carbon backbone, or a combination thereof, and
   wherein the substituents are selected from the group consisting of oxo, hydroxyl, carboxyl, amido, and amino groups.

5. The method of claim 1, wherein the active agent is present in an amount ranging from about 0.01 wt % to about 10 wt % of the second formulation.

6. The method of claim 1, wherein the active agent is present in an amount ranging from about 0.5 to 3 wt % of the second formulation.

7. The method of claim 1, wherein the second formulation is in the form of a gel, cream or lotion.

8. The method of claim 1, wherein step (b) is repeated one or more times.

9. The method of claim 1, further comprising:
   (c) rinsing, shampooing, or conditioning the hair, or a combination thereof, wherein step (c) occurs subsequent to step (b).

10. The method of claim 1, wherein the active agent is selected from the group consisting of:

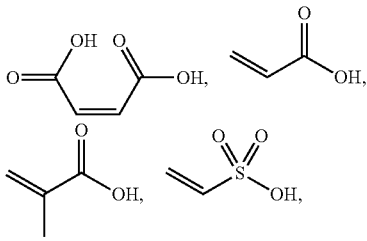

and simple salts thereof.

11. The method of claim 1, wherein the first formulation and the second formulation are mixed at the time of use and prior to application.

12. A method for bleaching hair comprising:
(a) applying to the hair a first formulation comprising a bleaching agent; and
(b) applying to the hair a second formulation comprising an active agent, wherein the second formulation does not contain a coloring agent, wherein the first and second formulations are in separate containers or compartments,
wherein the active agent has the formula:

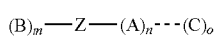

Formula II wherein Z is a linker or is absent;
m and n are each an integer independently selected from 1-6, and the sum of m+n is equal to or greater than 2; wherein A and B are covalently bonded to Z when Z is present;
B is a functional group capable of forming a covalent bond with a thiol or amine group and B is independently selected from the group consisting of:

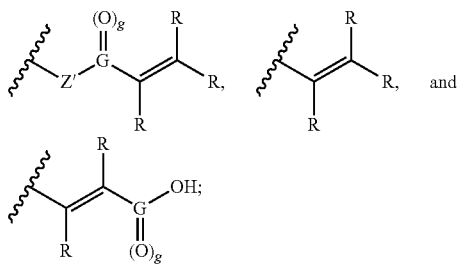

wherein R is independently selected from the group consisting of hydrogen, $C_{1-6}$ alkyl groups, aryl groups, or an ionizable functional groups and Z' is oxygen (O), NH or is absent, and G is carbon (C) and g is 1, or G is sulfur (S) and g is 2;
A is an ionizable functional group which is independently selected from the group consisting of: —COOH, —SO$_3$H, —PO$_3$H$_2$, —N(R$^1$)$_2$,—N(R$^1$)$_3$; wherein R$^1$ is independently selected from the group consisting of a hydrogen, alkyl, alkenyl, alkenyl, cycloalkyl, aryl, heterocycloalkyl and heteroaryl groups; wherein each R$^1$ is independently unsubstituted or substituted with one or more substituents; and
C contains an ionic group and a functional group capable of forming a covalent bond with a nucleophile, and has a charge opposite to that of the ionizable group A, and o is an integer value independently selected from 1-6, such that the sum of charges of C and A is zero; and
wherein step (a) occurs simultaneously with step (b).

13. The method of claim 12, wherein the linker Z is an alkyl group, alkenyl group, cycloalkyl group, cycloalkenyl group, aryl group, heterocycloalkyl group, or heteroaryl group,
wherein the alkyl, alkenyl, cycloalkyl, cycloalkenyl, aryl, heterocycloalkyl, or heteroaryl group is unsubstituted or substituted one or more times by a halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, (—COO$^-$), primary amide, secondary amide, —(C(O)NR$^1$R$^2$, —NR$^1$R$^2$, —NR$^1$S(O)$_2$R$^2$, NR$^1$C(O)R$^2$, —S(O)$_2$R$^2$ , —SR$^1$, —S(O)$_2$NR$^1$R$^2$, —SOR$^1$, or —SOOR$^1$;
wherein R$^1$ and R$^2$ are each independently selected from the group consisting of a hydrogen, alkyl group, alkenyl group, alkynyl group, cycloalkyl group, aryl group, heterocycloalkyl, and heteroaryl group, wherein each of R$^1$ and R$^2$ is independently unsubstituted or substituted with one or more substituents.

14. The method of claim 12, wherein the linker Z is a $C_{1-4}$ alkyl group.

15. The method of claim 14, wherein the alkyl group is substituted with one or more substituents replacing a hydrogen on one or more carbons of the alkyl hydrocarbon backbone or the alkyl group is substituted with one or more heteroatoms within the hydrocarbon carbon backbone, or a combination thereof, and
wherein the substituents are selected from the group consisting of oxo, hydroxyl, carboxyl, amido, and amino groups.

16. The method of claim 12, wherein the active agent is:

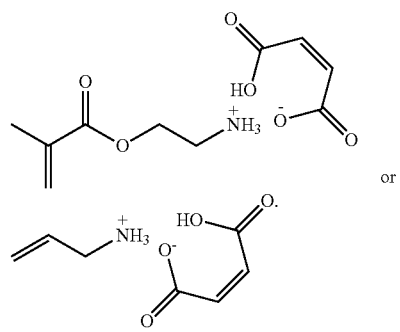

or

17. The method of claim 12, wherein the first formulation and the second formulation are mixed at the time of use and prior to application.

* * * * *

UNITED STATES PATENT AND TRADEMARK OFFICE
CERTIFICATE OF CORRECTION

PATENT NO. : 9,326,926 B2
APPLICATION NO. : 14/713885
DATED : May 3, 2016
INVENTOR(S) : Eric D. Pressly and Craig J. Hawker It is certified that error appears in the above-identified patent and that said Letters Patent is hereby corrected as shown below:

Specification,
Column 2, line 2, replace "Reactive Ito" to --Reaction I to--.
Column 2, lines 11-12, replace "that found hair" with --that found in hair--.
Column 7, line 19, replace "from about from about" to --from about--.
Column 7, line 40, replace "amines" with --amines.--.
Column 8, lines 64-65, replace "di-carboxylic acids" with --di-carboxylic acid--.
Column 10, lines 52-53, replace the term "di-carboxylic acids" with --di-carboxylic acid--.
Column 14, line 11, replace "semisythetic" with --semisynthetic--.
Column 18, line 53, introduce a line break between the term "agent" and the term "Subsequent".
Column 18, line 66, replace "washed about within about" with --washed within about--.
Column 19, line 64, replace "include" with --includes--.
Column 23, line 29, replace "hair was demonstrated" with --hair demonstrated--.
Column 23, line 63, replace "hair was demonstrated" with --hair demonstrated--.
Column 24, line 30, replace "peen" with --perm--.
Claims,
Claim 1, column 26, lines 10-11, replace "or an ionizable" with --and ionizable--.
Claim 1, column 26, line 15, replace "-N($R^1$)$_2$, -N($R^1$)$_3$" with -- -N($R^1$)$_2$, and -N($R^1$)$_3$--.
Claim 2, column 26, line 34, replace "-(O)$_2R^2$" with -- -S(O)$_2R^2$--.
Claim 7, column 26, line 61, replace "in the form of a gel, cream or lotion" with --in the form of a liquid, gel, cream, or lotion--.
Claim 12, column 27, lines 23-26, delete "wherein the second formulation does not contain a coloring agent, wherein the first and second formulations are in separate containers or compartments".
Claim 12, column 27, lines 56-57, replace "or an ionizable" with --and ionizable--.
Claim 12, column 27, line 62, replace "-N($R^1$)$_2$, -N($R^1$)$_3$" with -- -N($R^1$)$_2$, and -N($R^1$)$_3$--.
Claim 12, column 28, line 2, replace "alkenyl, alkenyl," with --alkenyl, alkynyl,--.
Claim 13, column 28, line 22, replace "-C(O)N$R^1R^2$" with -- -C(O)N$R^1R^2$--.

Signed and Sealed this
Ninth Day of August, 2016

Michelle K. Lee
*Director of the United States Patent and Trademark Office*